United States Patent [19]

Kapitanov et al.

[11] 4,286,598
[45] Sep. 1, 1981

[54] FORCEPS FOR ISOLATION OF PART OF BLOOD VESSEL DURING ANASTOMOSIS

[76] Inventors: Nikolai N. Kapitanov, ulitsa Iriny Levchenko, 3, kv.9; Natalia P. Petrova, 1 Novokuzminskaya ulitsa, 4, kv. 40; Vladimir V. Ippolitov, ulitsa Lavochkina, 6, korpus 2, kv. 143, all of Moscow, U.S.S.R.

[21] Appl. No.: 958,204

[22] Filed: Nov. 6, 1978

[51] Int. Cl.³ .................. A61B 17/00; A61B 17/12
[52] U.S. Cl. .................. 128/303 R; 128/326; 128/346
[58] Field of Search .............. 128/334 R, 334 C, 335, 128/326, 321, 303 R, 322, 346; 30/233; 81/425 A, 425 R, 426, 420, 418

[56] References Cited

U.S. PATENT DOCUMENTS

| | | | |
|---|---|---|---|
| 902,570 | 11/1908 | Ellis | 81/420 |
| 2,743,726 | 5/1956 | Grieshaber | 128/322 UX |
| 2,842,132 | 7/1958 | Soltero et al. | 128/322 |
| 3,369,550 | 2/1968 | Armao | 128/303.1 |
| 3,503,398 | 3/1970 | Fogarty et al. | 128/322 |
| 3,519,187 | 7/1970 | Kapitanov et al. | 227/19 |
| 3,575,038 | 4/1971 | Mallett | 128/326 |
| 3,779,248 | 12/1973 | Karman | 128/346 |
| 3,857,396 | 12/1974 | Hardwick | 128/335 |
| 3,916,908 | 11/1975 | Leveen | 128/346 |
| 3,921,640 | 11/1975 | Freeborn | 128/321 |
| 3,952,619 | 4/1976 | Cook | 81/425 A |

FOREIGN PATENT DOCUMENTS

| | | | |
|---|---|---|---|
| 1030351 | 5/1966 | United Kingdom | 227/19 |
| 1068536 | 5/1967 | United Kingdom | 128/334 |

Primary Examiner—Robert W. Michell
Assistant Examiner—C. W. Shedd
Attorney, Agent, or Firm—Fleit & Jacobson

[57] ABSTRACT

A forceps for isolation of a part of a blood vessel during anastomosis comprises hinged levers and an automatic lock to hold the levers in the closed position. There are rings at one end of each lever, by which the forceps is held. The other ends of the levers bear jaws arranged at an angle toward the levers. One jaw has a longitudinal groove open on the side facing the opposite jaw, while the other jaw is made in the form of a ridge whose width is the same as that of the groove so that the ridge enters the groove as the jaws are pulled together. Each jaw has a removable part that does not extend to the jaw ends.

This invention can advantageously be used to divide a part of a vessel into two parts along its longitudinal axis during anastomosis with mechanical suturing or ligation.

14 Claims, 9 Drawing Figures

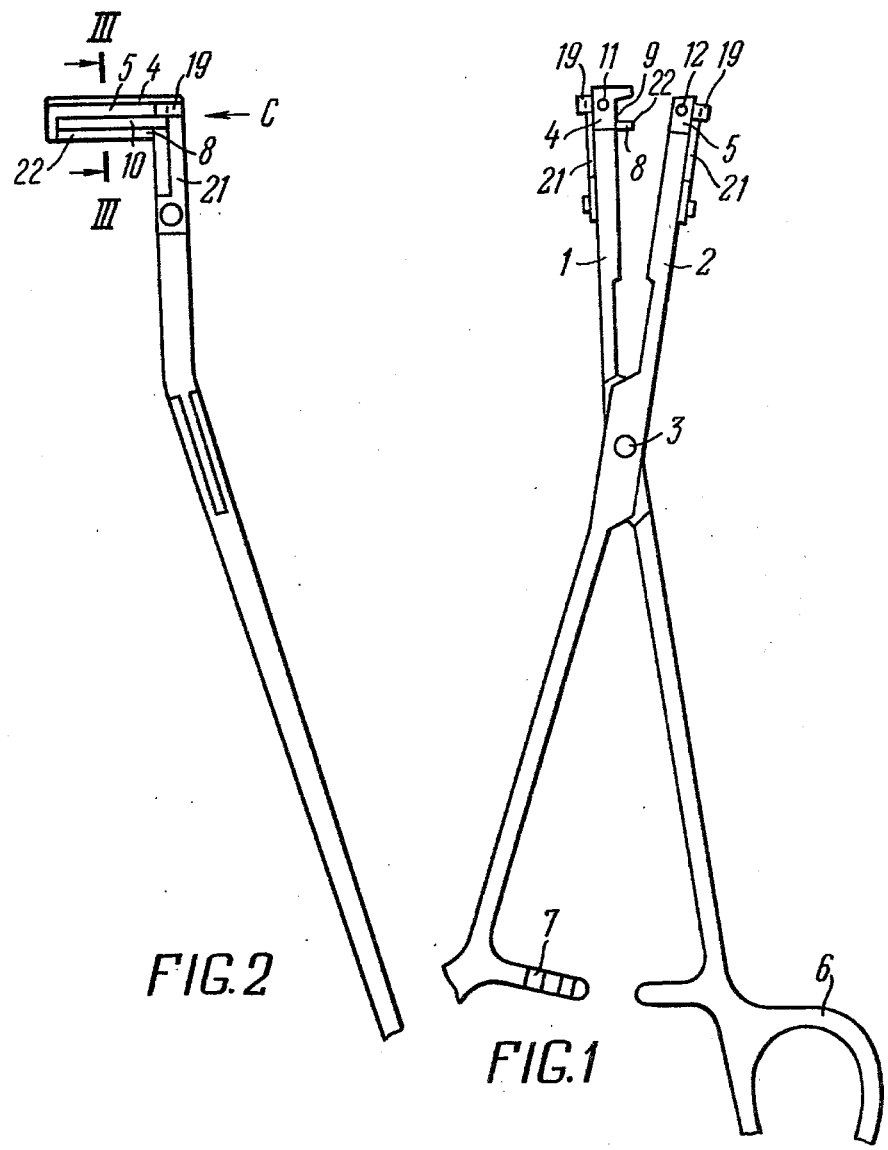

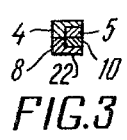 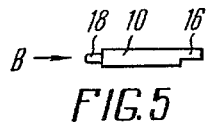 
FIG.3　　FIG.5　　FIG.7
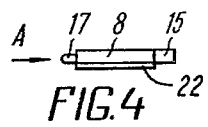 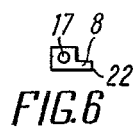
FIG.4　　FIG.6
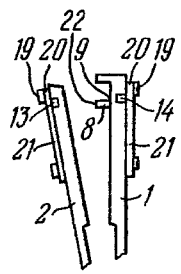 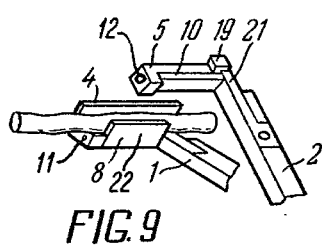 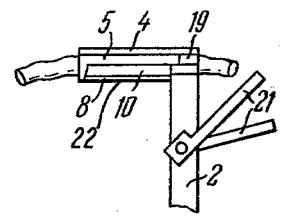
FIG.8　　FIG.9　　FIG.10
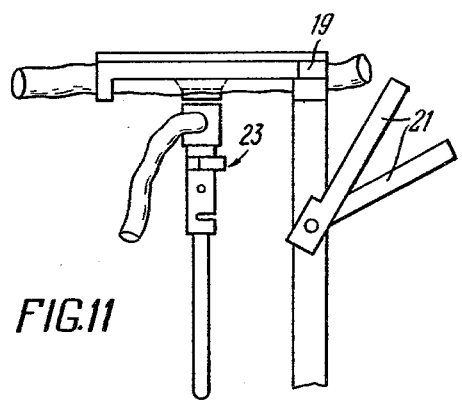
FIG.11

FORCEPS FOR ISOLATION OF PART OF BLOOD VESSEL DURING ANASTOMOSIS

FIELD OF THE INVENTION

This invention relates to medical equipment, and more particularly it relates to forceps for isolation of parts of vessels during their anastomosis.

This invention can most advantageously be used to divide a blood vessel into two parts along its longitudinal axis to suture vessels mechanically or by ligation.

Known in the prior art is a forceps for isolation of a small part of a large vessel, comprising hinged levers provided with two rounded jaws at their ends, arranged at an angle to said levers, two rings at their other ends, that serve to hold the forceps, and an automatic lock to fix the forceps in the closed position.

The forceps for isolation of a small part of a large blood vessel operate as follows.

The jaws are applied onto a particular part of a large blood vessel, the levers are pulled to compress the blood vessel, and the automatic lock holds the forceps in the closed position. The part of the vessel is isolated on the inner side of the jaws.

The known forceps can be used to isolate parts of large vessels and fails to isolate parts of small vessels, since smaller vessels, filled with blood, slip off the sides of the jaws or bends in either direction when captured by the jaws.

SUMMARY OF THE INVENTION

It is an object of the invention to provide forceps for isolation of a part of a vessel during anastomosing, that will hold smaller vessels.

Another object of the invention is to provide forceps that can be used for more accurate isolation of a part of the captured vessel.

The present invention resides in that, in forceps for isolation of a part of a blood vessel during anastomosis, comprising hinged levers, two ends of which bear jaws to hold the vessel, said ends being arranged at an angle, for instance, an angle of 90°, to the levers, while the other two ends bear rings to hold the forceps closed, and an automatic lock intended to fix the forceps in the closed position, a removable part is installed longitudinally on one of the jaws, said removable part forming a groove together with said jaw, said groove being open toward the other jaw, said other jaw being provided with another longitudinally installed part that forms a ridge together with said other jaw, the width of the ridge being equal to that of the groove so that the ridge enters the groove as the jaws are closed.

The forceps of this design securedly fix the vessel inside the box-shaped part of the jaws and keep it from slipping off the jaws or bending in any direction.

Moreover, the removable parts of the jaws ensure more accurate isolation of the required part of the fixed vessel.

In the end-to-side anastomosis of vessels with the known apparatus for suturing vessels and prostheses (U.S. Pat. No. 3,519,187 and British Pat. No. 1,030,351), the proposed forceps can be used to divide the vessel into two parts so that the tetrahedral part of the suturing apparatus can be inserted into the isolated part of the vessel, and the vessel sides can be sutured by the edge of the incised part of the isolated vessel, without narrowing the lumen of the sutured vessel. If the tetrahedral part of the suturing apparatus is inserted into the vessel without proposed forceps for isolation of a part of a vessel during anastomosing, the tetrahedral part rests against the inner wall of the vessel and the vessel is not sutured by the incised edge but by the middle (or even farther) part of the vessel, which narrows the satured vessel to decrease the blood flow through it. The proposed forceps can be used to suture vessels by end-to-side ligation, envoluting lesser parts of the vessel, without narrowing the vessel diameter.

BRIEF DESCRIPTION OF THE DRAWINGS

For a better understanding of the invention, it will be described in greater detail with reference to the appended drawings in which:

FIG. 1 shows forceps for isolation of a part of a blood vessel during anastomosis, according to the invention in the open position (side view);

FIG. 2 shows the forceps for isolation of a part of a blood vessel during anastomosis, according to the invention, in the closed position (front view);

FIG. 3 is a cross-sectional view of the jaws, taken along line III—III in FIG. 2;

FIG. 4 shows the removable part of the lower jaw, according to the invention;

FIG. 5 shows the removable part of the upper jaw, according to the invention;

FIG. 6 shows detail A of FIG. 4;

FIG. 7 shows detail B of FIG. 5;

FIG. 8 shows detail C of FIG. 2;

FIG. 9 shows the forceps in the open position with a blood vessel bedded in the lower jaw;

FIG. 10 shows a blood vessel held between the jaws;

FIG. 11 is an enlarged view of the forceps holding an isolated part of a blood vessel with a suturing part of the apparatus inside the vessel.

DETAILED DESCRIPTION OF THE INVENTION

The proposed forceps for isolation of a part of a blood vessel during anastomosis comprises levers 1 and 2 (FIGS. 1, 8, 9) hinged by a pin 3 (FIG. 1). One end of the levers 1 and 2 (FIGS. 1, 8, 9) bears jaws 4 and 5 (FIGS. 1, 2, 3, 9, 10) which are arranged at an angle to the levers and are intended to hold the blood vessel. The other ends of the levers bear rings 6 (FIG. 1). An automatic lock 7 (FIG. 1) serves to hold the jaws of the forceps in the closed position. A removable part 8 (FIGS. 1, 2, 3, 4, 6, 8, 9, 10) is installed on the jaw 4 (FIGS. 1, 2, 3, 9, 10). This removable part portion 22 does not extend to the end of the jaw 4 (FIGS. 1, 2, 3, 9, 10) and forms a groove 9 (FIGS. 1,8) together with the jaw, said groove being open toward the opposite jaw 5 (FIGS. 1, 2, 3, 9, 10). The jaw 5 has a removable part 10 (FIGS. 1, 2, 3, 9, 10) that does not extend to the end of the jaw either. Together with its removable part 10 (FIGS. 2, 3, 5, 7, 9, 10) the jaw 5 forms a ridge whose width is the same as that of the groove 9 (FIGS. 1 and 8) so that the ridge can enter the groove as the jaws are closed.

The ends of the jaws 4 and 5 (FIGS. 1, 2, 3, 9, 10) have holes 11 and 12 (FIG. 1) and the levers 1 and 2 (FIGS. 1, 2, 8, 9, 10) have slots 13 and 14 (FIG. 8). The removable parts 8 (FIGS. 1, 2, 3, 4, 6, 8, 9, 10) and 10 (FIGS. 2, 3, 5, 7, 9, 10) have respective protrusions 15 (FIG. 4) and 16 (FIG. 5) and pins 17 (FIGS. 4 and 6) and 18 (FIGS. 5 and 7). Jaws 4 and 5 (FIGS. 1, 2, 3, 9, 10) have protrusions 19 (FIGS. 1, 2, 8, 9, 19, 11) with slots 20 (FIG. 8), and movable plates 21 (FIGS. 1, 2, 8, 9, 10, 11) that enter the slots 20 (FIG. 8) of protrusions 19 (FIGS. 1, 2, 8, 9, 10, 11).

The pin 17 of the removable part 8 (FIGS. 4 and 6) enters the hole 11 (FIGS. 1 and 9), and the protrusion 15 (FIG. 4) engages the slot 14 (FIG. 8) and is forced by the plate 21 provided on the lever 1 (FIGS. 1 and 8). The end of the plate 21 engages the slot 20 of the protrusion 19 on the lever 1 (FIGS. 1 and 8), locking the removable part 8 (FIGS. 1, 8, 9, 10 and 11) in the closed position. The removable part 10 (FIGS. 2, 3, 5, 7, 9 and 10) has its pin 18 (FIGS. 5 and 7) engaging the hole 12 (FIGS. 1 and 9), while the protrusion 16 (FIG. 5) enters the slot 13 (FIG. 8) and is forced by the turnable plate 21 on the lever 2 (FIGS. 1, 8, 9, 10 and 11). The end of the plate 21 enters the slot 20 of the protrusion 19 on the lever 2 (FIGS. 1, 8, 9, 10 and 11).

FIG. 1 shows the forceps for isolation of a part of a blood vessel for anastomosis, prepared for operation.

The levers 1 and 2 are set apart by separating the rings 6 (FIG. 1). A vessel of a small diameter is placed in the groove 9 of the jaw 4, as shown in FIG. 9, and the other jaw 5, with the removable part 10, holds the vessel tight. Now, the automatic lock 7 (FIG. 1) is closed to fix the forceps in the closing position. Blood is thus displaced from the compressed part of the vessel. The tilting plates 21 (FIG. 10) are removed from the slots 20 (FIGS. 8 and 10), the removable parts 8 and 10 (FIG. 10) are dismantled to release the part of the vessel divided along its longitudinal axis. The other part of the vessel remains fixed between the jaws 4 and 5. The isolated part of the vessel is then incised longitudinally and a tetrahedral part of the suturing apparatus 23 (FIG. 11) is inserted into the incised vessel. The vessel is then sutured.

What is claimed is:

1. A surgical instrument for treating a tubular body member, vessel, duct, or the like, by clamping portions of the tubular body member at longitudinally spaced regions while providing access to a portion of the body member between the clamped portions comprising:
   a pair of jaws;
   means for opening and closing said jaws;
   a first of said jaws defining a channel for receiving a tubular body member to be clamped, a second of said jaws being shaped to fit into and substantially close the top of said channel to define a longitudinally-extending bounded space within which a tubular body member is to be confined;
   said jaws mutually coacting upon closure to provide clamping action suitable for closing off a tubular body member at two longitudinally-spaced regions, with at least a portion of the bounded space located between the clamping regions, so that, when a tubular body member is positioned in the bounded space and the jaws are closed, longitudinally spaced portions of the tubular body member are closed off, a portion of one of said jaws located between the clamping regions and partly defining the bounded space being movable with respect to the remainder of said one of said jaws and removable from said bounded space to allow access to the bounded space located between the clamping regions whereby that portion of a tubular body member located between said clamping regions is accessible for treatment.

2. A surgical instrument according to claim 1, wherein said movable portion of said one of said jaws is removable from said one of said jaws.

3. A surgical instrument according to claim 2, wherein said one of said jaws is said first jaw and wherein the removable portion forms a firt side wall of the channel, a fixed portion of said first jaw forming a base and a second side wall of the channel.

4. A surgical instrument according to claim 3, wherein said removable portion has a generally planar section defining the first side wall and portions protruding from opposite ends of the planar section, and wherein the base of said fixed portion has a recessed section for receiving the removable portion, openings being formed in the base for receiving the protruding portions, at least one of said openings forming an open slot, said apparatus further comprising means for closing the slot so that a protruding portion received in the slot is retained therein.

5. A surgical instrument according to claim 2, wherein said one of said jaws is said second jaw.

6. A surgical instrument according to claim 5, wherein the removable portion of said second jaw has a section cooperating with a fixed portion of said second jaw to substantially close the top of said bounded space and portions protruding from opposite ends of said section, the fixed portion having openings formed therein for receiving the protruding portions, at least one of said openings forming an open slot, said apparatus further comprising means for closing the slot so that a protruding portion received in the slot is retained therein.

7. A surgical instrument according to claim 1, wherein portions of both jaws located between the clamping regions and partly defining the bounded space are movable with respect to remaining portions of the respective jaws to allow access to the bounded space located between the clamping regions.

8. A surgical instrument according to claim 7, wherein said movable portions of said jaws are removable from said jaws.

9. A surgical instrument according to claim 1, wherein said means for opening and closing said jaws comprises a pair of pivotally interconnected levers, said jaws being located at ends of said levers.

10. A surgical instrument according to claim 9, wherein said levers have portions extending transversely to the bounded space located adjacent said jaws and wherein said jaws are co-planar with and perpendicular to said transversely-extending portions.

11. A surgical instrument according to claim 10, wherein portions of both jaws located between the clamping regions and partly defining the bounded space are removable to allow access to the bounded space located between the clamping regions.

12. A surgical instrument according to claim 11, wherein said removable portions of said jaws have sections thereof partially defining the bounded space and portions protruding from said sections, and wherein fixed portions of each of said jaws have openings formed therein for receiving the protruding portions, one of said openings being adjacent a respective one of said levers and forming an open slot, said apparatus further comprising means for closing the slot so that a protruding portion received in the slot is retained therein.

13. A surgical instrument according to claim 12, wherein said means for closing comprises plates pivotally mounted in respective ones of said levers, said plates being movable between positions closing the slots and positions in which the slots are open.

14. A hemostatic forceps for isolating and occluding a portion of a tubular body member during anastomosis which has two hinged levers having proximal and distal ends and each lever being formed of three portions, a handle portion, a jaw portion and a connecting portion which unites the handle and jaw portions, said levers being pivoted at the juncture of said handle portions and said connecting portion, said handle portions each being provided at their proximal end with a ring for holding the forceps, and each of said levers including a lock member located intermediately between said ring and said distal end of said lever and extending from said lever towards the other said lock member, said lock member being mutually engagable when said handle portions are pivoted towards one another and when engaged said lock members retain said jaw portions in a coapted mutual relation; said connecting members contain a curved portion in a closely spaced relation to said pivot, said distal end of said connecting members being angled laterally from the plane in which the handle portions pivot; said jaw portions extend substantially perpendicularly from the corresponding sides of the distal ends of the connecting portions; wherein the improvement comprises: a removable coapting part disposed within and oriented lengthwise in each of the jaw portions, a first removable part is generally U shaped in cross section and forms three sides of a groove which extends lengthwise of the associated jaw portion, a second removable part associated with the other jaw portion is generally rectangular in cross section and is sized so as to project into substantially the entire length of the U shaped groove of the first removable part when the jaw portions are closed; each of said removable parts has a first and a second retaining means for positioning said removable parts within the respective jaw portions, said first retaining means is a pintle and gudgeon coupling at one end of said jaw portion, said second retaining means is a plate pivotally mounted in such fashion that the other end of said removable part is engagable by said plate, whereby rotation of said plate disengages said removable part and permits removal thereof; the combined result of the various coapting elements is to occlude a tubular body member which is placed in said groove whereby substantially all body fluids residing in the tubular member are squeezed out of that portin of the tubular member which is engaged by said removable parts prior to complete occlusion of the tubular member by said jaw portions at both the proximal and distal ends of said removable parts; removal of said removable parts permits access to that portion of said tubular member which is substantially free of contained body fluids for further operative procedures; and lock members retain said jaw portions in the coapting relationship.

* * * * *